United States Patent
Komori et al.

(10) Patent No.: US 11,946,847 B2
(45) Date of Patent: Apr. 2, 2024

(54) EXTRACELLULAR POTENTIAL MEASUREMENT DEVICE

(71) Applicants: NOK CORPORATION, Tokyo (JP);
THE UNIVERSITY OF TOKYO, Tokyo (JP)

(72) Inventors: Takayuki Komori, Fujisawa (JP);
Keiichi Miyajima, Fujisawa (JP);
SooHyeon Kim, Tokyo (JP); Teruo Fujii, Tokyo (JP); Shinji Okawa, Tokyo (JP)

(73) Assignees: NOK CORPORATION (JP); THE UNIVERSITY OF TOKYO (JP)

( * ) Notice: Subject to any disclaimer, the term of this patent is extended or adjusted under 35 U.S.C. 154(b) by 143 days.

(21) Appl. No.: 17/772,219

(22) PCT Filed: Oct. 1, 2020

(86) PCT No.: PCT/JP2020/037452
§ 371 (c)(1),
(2) Date: Apr. 27, 2022

(87) PCT Pub. No.: WO2021/095393
PCT Pub. Date: May 20, 2021

(65) Prior Publication Data
US 2022/0397511 A1    Dec. 15, 2022

(30) Foreign Application Priority Data

Nov. 14, 2019  (JP) ................................. 2019-205942
Nov. 14, 2019  (JP) ................................. 2019-205943

(51) Int. Cl.
*G01N 15/10* (2006.01)
*C12M 1/34* (2006.01)
(Continued)

(52) U.S. Cl.
CPC ......... *G01N 15/1031* (2013.01); *C12M 41/28* (2013.01); *G01N 2015/0065* (2013.01)

(58) Field of Classification Search
CPC ....... G01N 15/1031; G01N 2015/0065; G01N 33/48728; C12M 41/28; C12M 41/46; B01L 2300/0645; B01L 2300/0663
See application file for complete search history.

(56) References Cited

U.S. PATENT DOCUMENTS 6,132,683 A   10/2000  Sugihara et al.
6,803,019 B1  10/2004  Bjornson et al.
(Continued)

FOREIGN PATENT DOCUMENTS

JP   2001-520377 A   10/2001
JP   2002-523726 A    7/2002
(Continued)

OTHER PUBLICATIONS

International Search Report (in English and Japanese) issued in PCT//JP2020/037452, dated Dec. 22, 2020; ISA/JP (6 pages).
(Continued)

*Primary Examiner* — Giovanni Astacio-Oquendo
*Assistant Examiner* — Zannatul Ferdous
(74) *Attorney, Agent, or Firm* — Harness, Dickey & Pierce, P.L.C.

(57) ABSTRACT

An extracellular potential measurement device includes multiple insulating films each of which is made from an electric insulating material, the insulating films being stacked and bonded to each other; and multiple electrode wires each of which is made from an electroconductive material, the electrode wires being arranged in multiple heights. Each of the electrode wires is interposed between an upper insulating film and a lower insulating film. Each of the insulating films, except for a lowermost insulating film, has (Continued)

an opening penetrating the insulating film. The opening in a lower insulating film has a size that is less than that of the opening in an upper insulating film, the openings in the insulating films being overlapped to form a recess having a size reducing downward, the recess being adapted to store a collection of cells. Each of the electrode wires has an end that is located near an opening in an insulating film that is immediately below the electrode wire, the ends being exposed in the recess.

14 Claims, 5 Drawing Sheets

(51) Int. Cl.
    *G01N 15/1031*    (2024.01)
    *G01N 15/00*    (2006.01)

(56) References Cited

U.S. PATENT DOCUMENTS

| | | |
|---|---|---|
| 2009/0145780 A1 | 6/2009 | Sasaki et al. |
| 2010/0304423 A1 | 12/2010 | Asai et al. |
| 2011/0021943 A1 | 1/2011 | Lacour et al. |
| 2012/0119762 A1 | 5/2012 | Morimoto et al. |
| 2013/0162276 A1* | 6/2013 | Lee .................. G01R 1/07378 29/830 |
| 2013/0230881 A1 | 9/2013 | Yasuda et al. |
| 2015/0233890 A1 | 8/2015 | Urisu et al. |
| 2015/0377763 A1* | 12/2015 | Brun .................. G01N 27/221 324/693 |
| 2016/0153935 A1* | 6/2016 | Nishigaki .......... G01N 15/1459 204/601 |
| 2017/0370827 A1 | 12/2017 | Wohlstadter et al. |
| 2019/0049399 A1* | 2/2019 | Ogura .................. G01N 33/48 |

FOREIGN PATENT DOCUMENTS

| | | |
|---|---|---|
| WO | 1999-019717 A1 | 4/1999 |
| WO | 1999-034202 A1 | 7/1999 |
| WO | 2009-013876 A1 | 1/2009 |
| WO | 2009-038079 A1 | 3/2009 |
| WO | 2011-010721 A1 | 1/2011 |
| WO | 2012-043820 A1 | 4/2012 |
| WO | 2012-072822 A1 | 6/2012 |
| WO | 2014-045618 A1 | 3/2014 |
| WO | 2017-157874 A1 | 9/2017 |

OTHER PUBLICATIONS

Extended European Search Report for corresponding Application No. 20886240.9 dated Jan. 26, 2023 (9 Pages).

* cited by examiner

EXTRACELLULAR POTENTIAL MEASUREMENT DEVICE

CROSS REFERENCE TO RELATED APPLICATIONS

This application is a U.S. National Phase Application under 35 U.S.C. 371 of International Application No. PCT/JP2020/037452, filed on Oct. 1, 2020, which claims priority to Japanese Patent Application No. 2019-205942, filed on Nov. 14, 2019, and Japanese Patent Application No. 2019-205943, filed on Nov. 14, 2019. The entire disclosures of the above applications are expressly incorporated by reference herein.

BACKGROUND

Technical Field

The present invention relates to extracellular potential measurement devices.

Related Art

In recent years, devices for measuring an extracellular potential of cell masses or spheroids, each of which is a collection of cells, in vitro have been developed (International Publication WO 2009/038079 and International Publication WO 2011/010721). Analyses of extracellular potentials are useful for evaluating drug effects and/or side effects on cells.

The cell masses, organoids, or spheroids, each of which is a collection of cells, have a three-dimensional structure, and therefore, it is desirable to be able to measure electric potentials at multiple points in different heights. Furthermore, it is desirable that a device for measuring electric potentials can be easily manufactured. Therefore, there is a demand for an extracellular potential measuring device that can measure potentials at multiple points in different heights of a collection of cells and that can be easily manufactured.

On the other hand, one or more linear axons may extend from a cell mass, organoid or spheroid that is a collection of cells related to neurons. Measuring potentials of axons as well as cell collections may contribute to analyses of the behavior of a nervous system in vivo. Therefore, there is a demand for an extracellular potential measurement device that can measure not only potentials of a collection of cells but also potentials of axons.

Accordingly, the present disclosure solves any of the above problems.

SUMMARY

In accordance with an aspect of the disclosure, an extracellular potential measurement device includes multiple insulating films each of which is made from an electric insulating material, the insulating films being stacked and bonded to each other; and multiple electrode wires each of which is made from an electroconductive material, the electrode wires being arranged in multiple heights. Each of the electrode wires is interposed between an upper insulating film and a lower insulating film. Each of the insulating films, except for a lowermost insulating film, has an opening penetrating the insulating film. The opening in a lower insulating film has a size that is less than that of the opening in an upper insulating film, the openings in the insulating films being overlapped to form a recess having a size reducing downward, the recess being adapted to store a collection of cells. Each of the electrode wires has an end that is located near an opening in an insulating film that is immediately below the electrode wire, the ends being exposed in the recess.

In this aspect, a three-dimensional collection of cells is stored in the recess with a varying size reducing downward, which is provided by overlapping the openings of the multiple insulating films stacked. An end of each of the electrode wires interposed between upper and lower insulating films is located near the opening in the insulating film immediately below it and is exposed in the recess, so that ends of the multiple electrode wires can be in contact with the three-dimensional collection of cells. The multiple electrode wires are arranged in multiple heights, i.e., in multiple layers, so that electric potentials at multiple points in different heights of the collection of cells can be measured.

In addition, in the extracellular potential measurement device according to the aspect, multiple insulating films having openings are joined together to form the recess with a varying size reducing downward, which is suitable for storing a three-dimensional collection of cells, and electrode wires interposed between the multiple insulating films can be located at multiple heights. Accordingly, it is easy to manufacture the extracellular potential measurement device that can measure potentials at multiple points in different heights of the three-dimensional collection of cells. By laminating a large number of insulating films, it is possible to increase the number of heights in which electrode wires are provided and the number of electrode wires, so that detailed analyses of the collection of cells can be conducted.

An extracellular potential measurement device according to another aspect of the present disclosure includes a sheet including multiple insulating films each of which is made from an electric insulating material, the insulating films being stacked and bonded to each other, the sheet further including a recess adapted to store a collection of cells and a groove connected to the recess, the groove being adapted to store a linear axon extending from the collection of cells; and multiple electrode wires interposed between the insulating films of the sheet. Each of the electrode wires has an end exposed in the recess so as to be brought into contact with the collection of cells. At least one electrode wire has an end exposed in the groove so as to be brought into contact with the axon.

In this aspect, in addition to potentials of a collection of cells, potentials of an axon extending from the collection of cells can be measured. By analyzing the potentials, it is possible to study in vitro models that are useful for estimating signal transduction in neurons in vivo, and to evaluate, for example, drug effects and/or side effects on neurons.

DETAILED DESCRIPTION

Hereinafter, with reference to the accompanying drawings, various embodiments according to the present invention will be described. It is of note that the drawings are not necessarily to scale, and certain features may be exaggerated or omitted.

Figure 1:
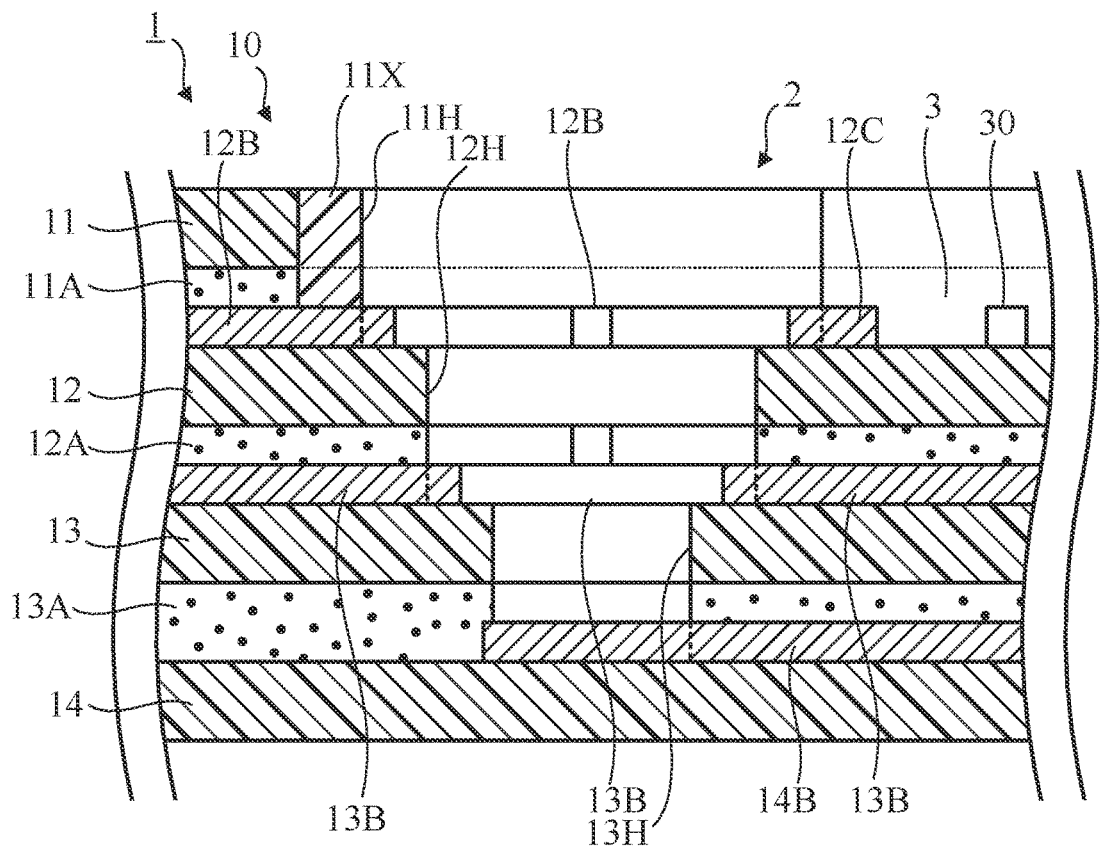
FIG. 1 is a cross-sectional view of an extracellular potential measurement device according to an embodiment of the present invention.

As shown in FIG. 1, an extracellular potential measurement device 1 includes a laminated structure having multiple electric insulating films 11, 12, 13, and 14 stacked one on top of the other, and adhesive layers 11A, 12A, and 13A that join the insulating films 11, 12, 13, and 14. More specifically, the insulating films 11 and 12 are bonded with the adhesive layer 11A, and the insulating films 11 and 12 are bonded with the adhesive layer 12A. The insulating films 12 and 13 are bonded with the adhesive layer 13A.

The insulating films 11, 12, 13, and 14 and the adhesive layers 11A, 12A, and 13A form a sheet 10. The sheet 10 has a recess 2, which will be described later, and a groove 3 connected to the recess 2.

The extracellular potential measurement device 1 further includes multiple electrode wires 12B, 12C, 13B, and 14B disposed in multiple heights, i.e., in multiple layers of the sheet 10. Each electrode wire is placed between upper and lower insulating films.

Figure 2:
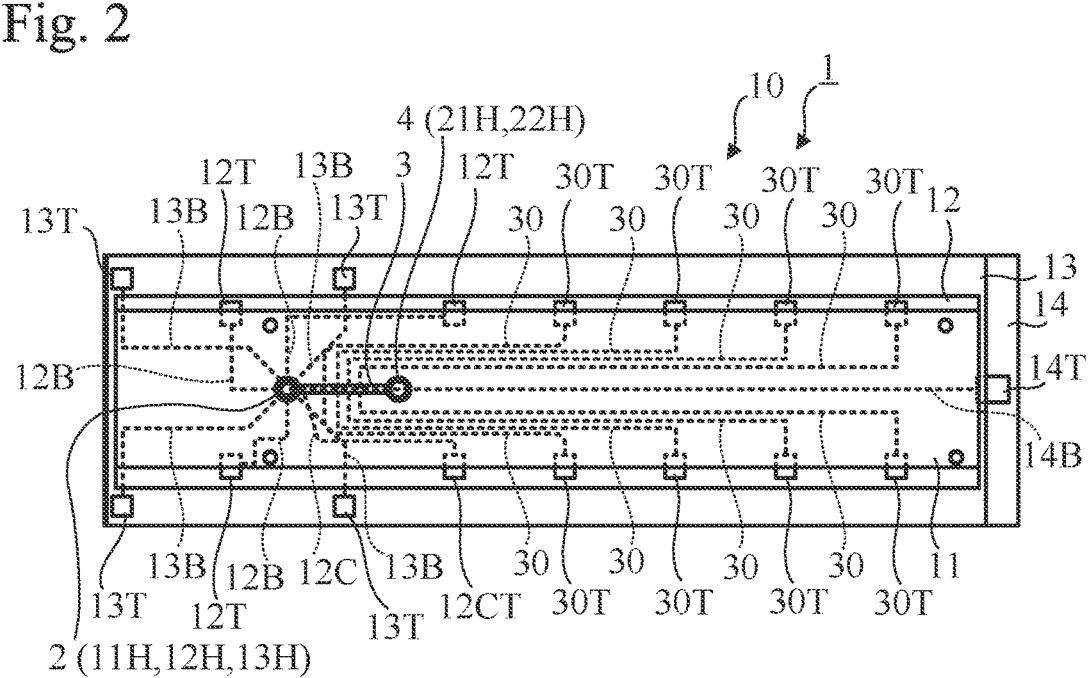
FIG. 2 is a plan view of the extracellular potential measurement device according to the embodiment.

As shown in FIGS. 1 and 2, except for the bottom-layer insulation film 14, each of the insulation films 11, 12 and 13 has a penetrating opening 11H, 12H, or 13H. Each of the openings 11H, 12H, and 13H has a circular shape. The openings 11H, 12H, and 13H are arranged approximately concentrically with each other.

The opening 13H in the insulating film 13 has a diameter, i.e., a size that is less than that of the opening 12H in the insulating film 12 immediately above it. The opening 12H in the insulating film 12 has a diameter, i.e., a size that is less than that of the opening 11H in the insulating film 11 immediately above it. When the multiple insulating films 11, 12, and 13 are stacked, the openings 11H, 12H, and 13H form the recess 2 that has an almost cone-shape or bowl-shape with a varying size reducing downward. However, the shapes of the openings 11H, 12H, and 13H are not limited to circular, but can be other shapes.

Each of the adhesive layers 11A, 12A, and 13A has an opening having the same shape and the same size as those of the opening in the insulating film immediately above it. The edge, i.e., the inner peripheral surface of the opening of each of the adhesive layers 11A, 12A, and 13A is aligned as much as possible with the edge, i.e., the inner peripheral surface of the opening of the insulating film immediately above it. However, some deviation between the inner surface of the opening of the adhesive layer and the inner surface of the opening of the insulating film is allowed.

Each of the insulating films 11, 12, 13, and 14 is made from an electric insulating material that has as little effect as possible on cells, such as polyimide. Each of the adhesive layers 11A, 12A, and 13A is also made from an electric insulating material that has as little effect as possible on cells. Although not absolutely necessary, it is preferable that the insulating films 11, 12, 13, and 14 and the adhesive layers 11A, 12A, and 13A are made from a transparent or semi-transparent material so that the electrode wires are visible.

Each of the electrode wires 12B, 12C, 13B, and 14B is made from an electroconductive material with high conductivity that has as little effect as possible on cells. For example, the electrode wires 12B, 12C, 13B, and 14B are formed from gold-plated copper wires.

An end of each of the multiple electrode wires are located near the openings in the insulating films immediately below the electrode wires and are exposed in the recess 2. More specifically, ends of electrode wires 12B and 12C are located near the opening 12H of the insulating film 12 immediately below the electrode wires 12B and 12C, and are exposed through the upper opening 11H. Ends of the electrode wires 13B are located near the opening 13H of the insulating film 13 immediately below the electrode wire 13B, and are exposed through the upper openings 11H and 12H.

An end of the electrode wire 14B interposed between the bottom-layer insulation film 14 and the second-lowermost-layer insulation film 13 traverses the entirety of the opening 13H in the second-lowermost-layer insulating film 13 in one direction. More specifically, the end of the electrode wire 14B extends along a diameter of the circular opening 13H and traverses the opening 13H. The end of the electrode wire 14B is exposed through the upper openings 11H, 12H, and 13H.

FIGS. 3 to 6 are plan views of the insulating films 11, 12, 13, and 14, respectively. FIG. 1 corresponds to the cross-section taken along line I-I in FIGS. 3 to 6.

Figure 3:
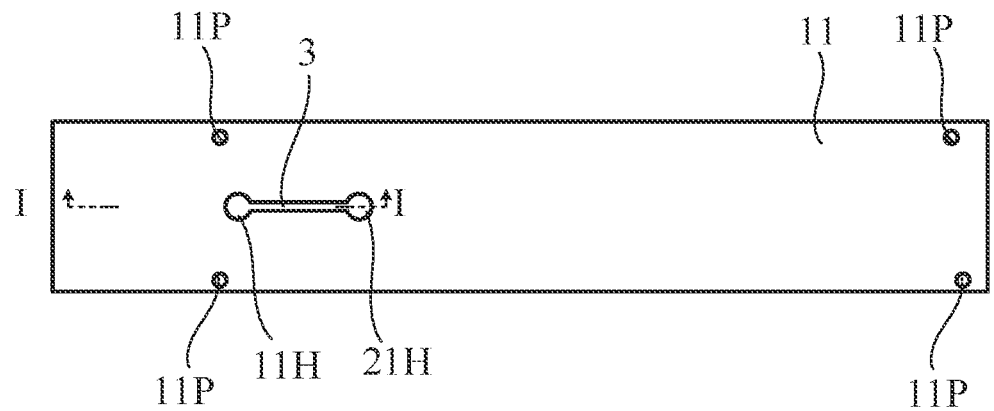
FIG. 3 is a plan view of a cover film of the extracellular potential measurement device according to the embodiment.

As shown in FIG. 3, the top-layer insulating film (cover film) 11 has the aforementioned opening 11H, another opening 21H having the same shape and the same size as those of the opening 11H, and a linear slit or groove 3 connecting the openings 11H and 21H. The openings 11H and 21H and the groove 3 penetrate the insulating film 11.

In addition, multiple through-holes 11P are formed in the insulating film 11 for positioning the insulating films 11, 12, 13, and 14 to be laminated.

Figure 4:
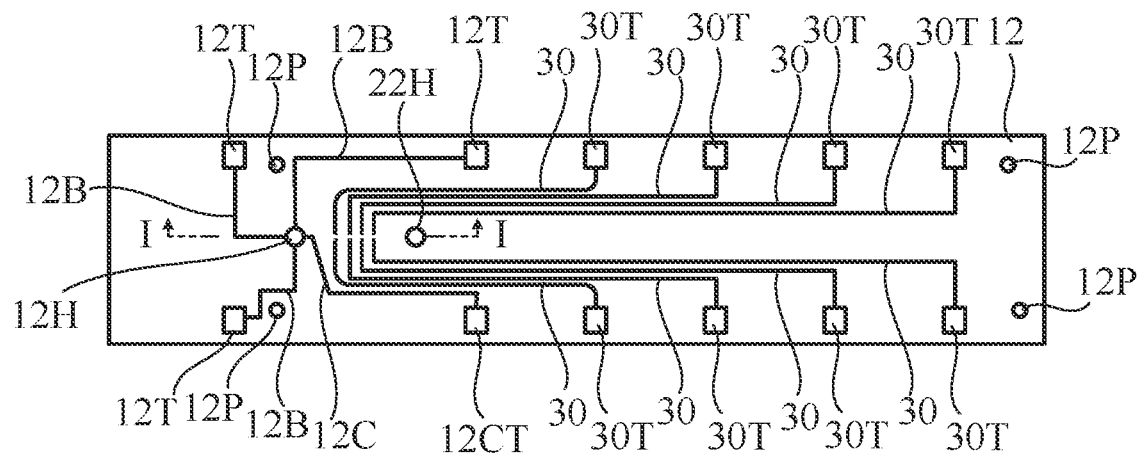
FIG. 4 is a plan view of a second-layer film and electrode wires thereon of the extracellular potential measurement device according to the embodiment.

As shown in FIG. 4, the insulating film 12 has the aforementioned opening 12H and another opening 22H having the same shape and the same size as those of the openings 12H. The openings 12H and 22H penetrate the insulating film 12. The opening 22H is almost concentric to the opening 21H of the insulating film 11. The opening 22H in the insulating film 12 has a diameter, i.e., a size that is less than that of the opening 21H in the insulating film 11 immediately above it. The opening 22H of insulating film 12 has a diameter, or size, smaller than the diameter, or size, of the opening 2H of insulating film 11 immediately above it.

When the insulating films 11 and 12 are stacked, the openings 21H and 12H form a recess with a varying size reducing downward.

In the insulating film 12, multiple through-holes 12P are formed for positioning the insulating films 11, 12, 13, and 14 to be laminated.

The aforementioned electrode wires 12B and 12C are formed on the upper surface of the insulating film 12. Wide connection terminals 12T and 12CT are formed at the ends of the electrode wires 12B and 12C, which are opposite to the ends near the opening 12H.

In addition, on the upper surface of the insulating film 12, multiple axon electrode wires 30, which will be described later, are formed. An end of each of the multiple axon electrode wires are located in the vicinity of a straight line connecting the openings 12H and 22H and are exposed in the groove 3 of the insulating film 11 immediately above. Wide connection terminals 30T are formed at the opposite ends of the axon terminal wires 30.

Each of the axon electrode wires 30 is formed from an electroconductive material with high conductivity that has as little effect as possible on cells. For example, the axon electrode wires 30 are formed from gold-plated copper wires.

Figure 5:
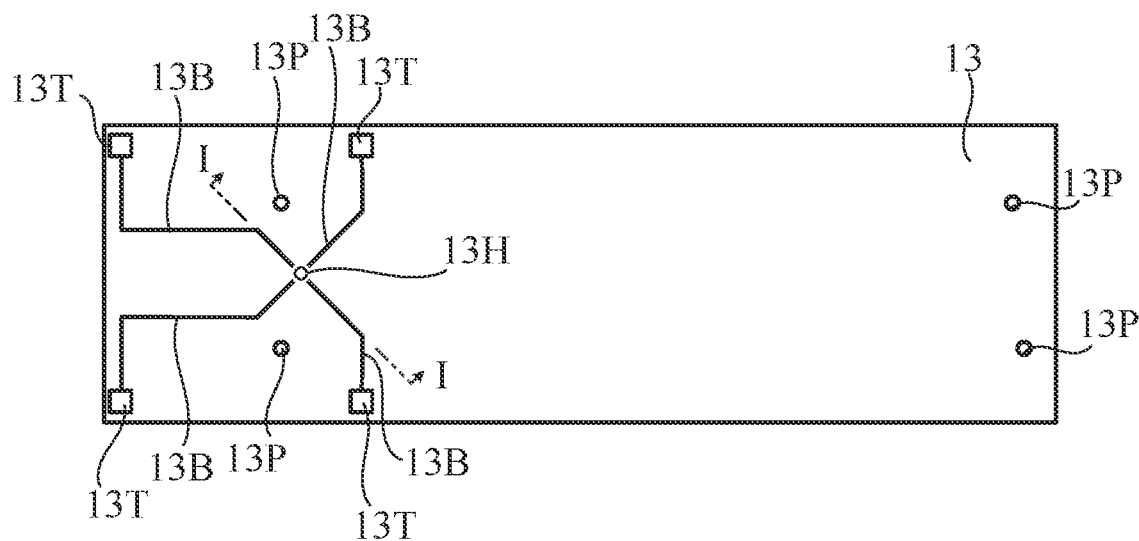
FIG. 5 is a plan view of a third-layer film and electrode wires thereon of the extracellular potential measurement device according to the embodiment.

As shown in FIG. 5, the aforementioned opening 13H is formed in the insulating film 13. The opening 13H penetrates the insulating film 13.

In addition, the insulating film 13 has multiple through-holes 13P for positioning the insulating films 11, 12, 13, and 14 to be laminated.

On the upper surface of the insulating film 13, the aforementioned electrode wires 13B are formed. Wide connection terminals 13T are formed at the ends of the electrode wires 13B, which are opposite to the ends near the opening 13H.

Figure 6:
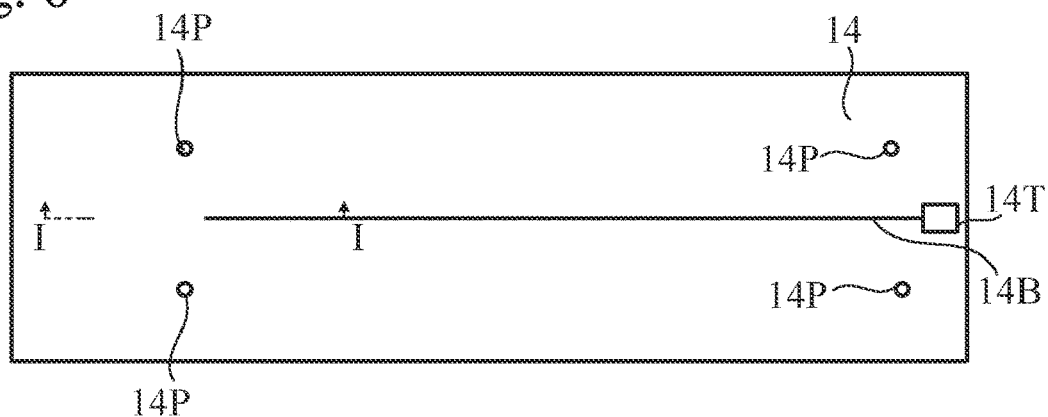
FIG. 6 is a plan view of a bottom-layer film and electrode wires thereon of the extracellular potential measurement device according to the embodiment.

As shown in FIG. 6, multiple through-holes 14P are formed in the insulating film 14 for positioning the insulating films 11, 12, 13, and 14 to be laminated.

On the upper surface of the insulating film 14, the aforementioned electrode wire 14 is formed. A wide connection terminal 14T is formed at the end of the electrode wire 14B, which is opposite to the end overlapping the opening 13H.

The holes and grooves in the insulating films can be formed by, for example, etching. The electrode wires can be formed on the insulating films by, for example, photolithography.

When joining insulating films 11, 12, 13, and 14 with adhesive layers 11A, 12A, and 13A, pins are inserted into the through-holes 11P, 12P, 13P, and 14B for positioning the insulating films 11, 12, 13, and 14.

The insulating film 11 and the insulating films 12, 13, and 14 having the electrode wires formed thereon are bonded with the adhesive layers 11A, 12A, and 13A, so that the extracellular potential measurement device 1 can be easily manufactured.

As shown in FIG. 2, the width of the insulating film 11 is less than that of the insulating film 12 immediately below it, and almost all of the electrode wires 12B, 12C, and 30 formed on the insulating film 12 are covered with and protected by the upper insulating film 11 However, the connection terminals 12T, 12CT, and 30T of the electrode wires 12B, 12C, and 30 are exposed at least in part. The width of the insulating film 12 is less than that of the insulating film 13 immediately below it, and almost all of the electrode wires 13B formed on the insulating film 13 are covered with and protected by the upper insulating film 12. However, the connection terminals 13T of the electrode wires 13B are exposed at least in part. The length of insulating film 13 is less than that of the insulating film 14 immediately below it, and almost all of the electrode wire 14B formed on insulating film 14 is covered with and protected by the upper insulating film 13. However, the connection terminal 14T of the electrode wire 14B is exposed at least in part.

Accordingly, the connection terminals 12T, 12CT, 30T, 13T, and 14T can be easily connected to a potential measurement device (not shown).

Figure 7:
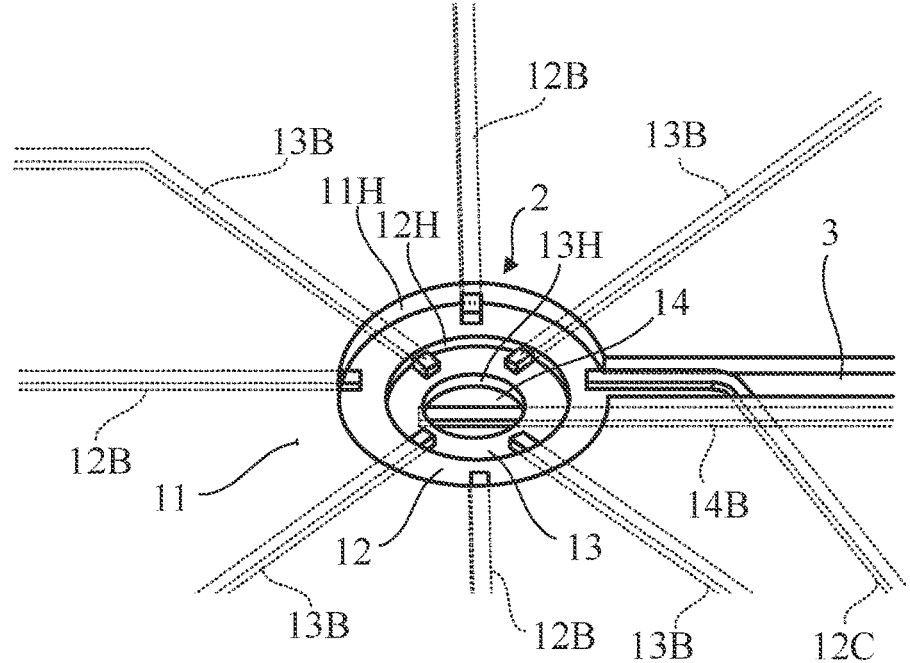
FIG. 7 is an enlarged perspective view of a part of the extracellular potential measurement device according to the embodiment.
Figure 8:
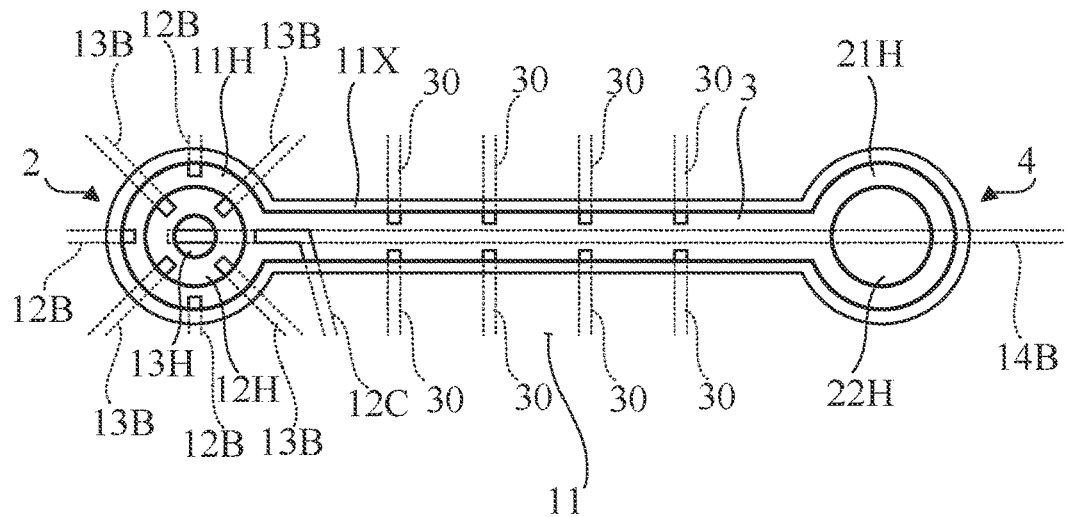
FIG. 8 is an enlarged plan view of a part of the extracellular potential measurement device according to the embodiment.

As shown in FIGS. 7 and 8, the ends of electrode wires 12B, 12C, and 13B extend radially relative to the recess 2. An end of the electrode wire 14B formed on the insulating film 14 extends in the groove 3 formed in the insulating film 12. The electrode wire 14B is bent, and portions other than the end are covered by the insulating film 14.

FIG. 8 shows the aforementioned opening 21H formed in the insulating film 11 and the aforementioned opening 22H formed in the insulating film 12. When the insulating films 11 and 12 are stacked, the openings 21H and 22H form a recess 4 that has an almost cone-shape or bowl-shape with a varying size reducing downward. However, the shapes of the openings 11H, 12H, and 13H are not limited to circular, but can be other shapes.

The openings 11H and 21H are connected by the linear slit or groove 3 formed in the insulating film 11. Ends of the multiple axon electrode wires formed on the insulating film 12 immediately below the groove 3 are exposed in the groove 3 in the insulating film 11.

To prevent the groove 3 from being filled with the adhesive layer 11A, and to improve the dimensional accuracy of the openings 11H and 21H, a portion 11X around the groove 3 and the openings 11H and 21H in the insulating film 11 are preferably formed by photolithography.

More specifically, first the insulating film 11 without the portion 11X (the insulating film 11 having a penetrating recess corresponding to the portion 11X) is formed. The recess can be formed in the insulating film 11 by, for example, etching.

Next, pins (not shown) are inserted into the through-holes 11P, 12P, 13P, 14P, so that the insulating films 11, 12, 13, and 14 are positioned, and the insulating films 11, 12, 13, and 14 are joined with adhesive layers 11A, 12A, and 13A.

Thereafter, the recess corresponding to the portion 11X is filled with an ultra-violet-curable resin, and a portion of the UV-curable resin other than the groove 3 and recesses 2 and 4 is exposed to an ultra-violet light to be cured. Furthermore, the groove 3 and the recesses 2 and 4 are formed by etching. In this way, the groove 3 and the openings 11H and 21H are formed, and at the same time, ends of the electrode wires are exposed.

The portion 11X formed in this way reaches not only the layer of the insulating film 11, but also the adhesive layer 11A as shown in FIG. 1. As shown in FIG. 8, ends of the axon electrode wires 30 penetrate the portion 11X.

In this embodiment, a three-dimensional collection of cells is stored in the recess 2 with a varying size reducing downward, which is provided by overlapping the openings 11H, 12H, and 13H of the multiple insulating films 11, 12, and 13 stacked. An end of each of the electrode wires 12B, 12C, and 13B interposed between upper and lower insulating films is located near the opening in the insulating film immediately below it and is exposed in the recess 2, so that ends of the multiple electrode wires 12B, 12C, and 13B can be in contact with the three-dimensional collection of cells. The multiple electrode wires 12B, 12C, and 13B are arranged in multiple heights, i.e., in multiple layers, so that electric potentials at multiple points in different heights of the collection of cells can be measured.

An end of the lowest electrode wire 14B traverses the entirety of the opening of the second-lowermost-layer insulating film 13, i.e., the bottom of the recess 2, in one direction. Accordingly, a large area of the end of the electrode wire 14B is exposed in the recess 2, and the collection of cells located in the recess 2 is likely to come into contact with the end of the electrode wire 14B. The electrode wire 14B, which has a high probability of contacting a collection of cells, can be preferably used as a reference electrode, for example. However, the reference electrode may be any one of the other electrode wires.

In the extracellular potential measurement device 1 according to the embodiment, multiple insulating films having openings 11H, 12H, and 13H, are joined together to form the recess 2 with a varying size reducing downward, which is suitable for storing a three-dimensional collection of cells, and electrode wires 12B, 12C, 13B, and 14B interposed between the multiple insulating films 11, 12, 13, and 14 can be located at multiple heights. Accordingly, it is easy to manufacture the extracellular potential measurement device 1 that can measure potentials at multiple points in different heights of the three-dimensional collection of cells. By laminating a large number of insulating films, it is possible to increase the number of heights in which electrode wires are provided and the number of electrode wires, so that detailed analyses of the collection of cells can be conducted.

The collection of cells disposed in the recess 2 may be a cell mass in vivo or a cell mass, an organoid, or a spheroid cultured in vitro.

Figure 9:
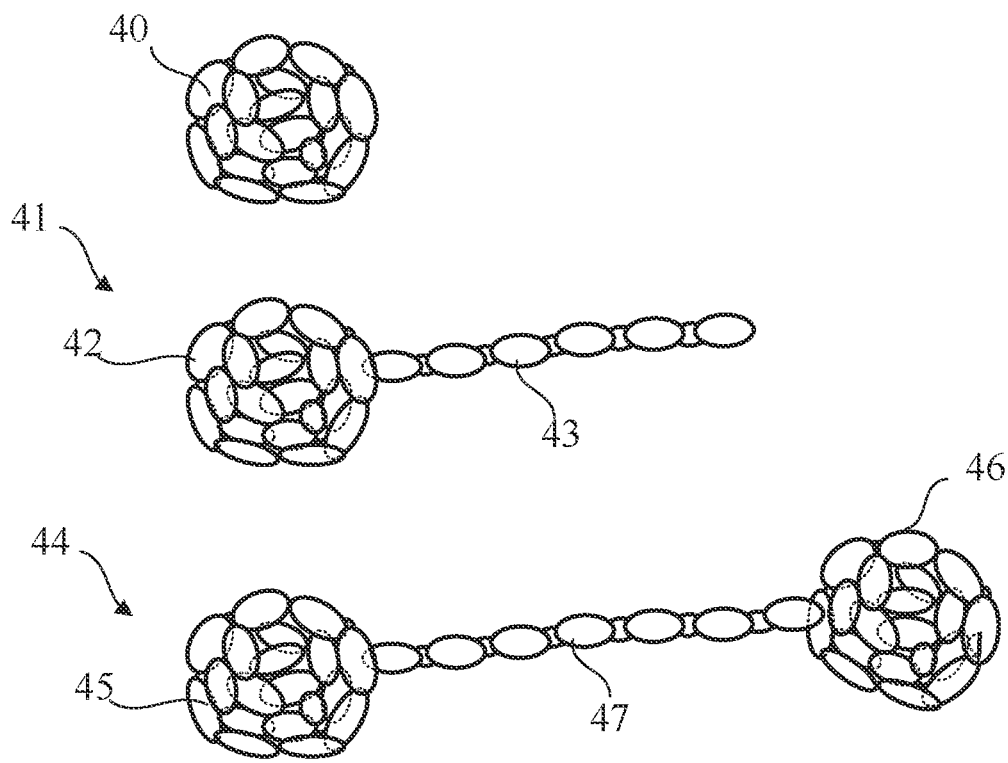
FIG. 9 is a diagram showing a plurality of examples of samples of collections of cells to be disposed in the extracellular potential measurement device according to the embodiment.

FIG. 9 shows a plurality of examples of samples that may be used for extracellular potential measurement using the extracellular potential measurement device 1. Sample 40 is a collection of cells that do not have axons. Sample 41 is a collection 42 of cells related to neurons and an axon 43 extending from the collection 42 of cells. Sample 44 has two collections 45 and 46 of cells related to neurons and an axon 47 connected to collections 45 and 46 of cells. Inside the recess 2 of the extracellular potential measurement device 1, any of sample 40, the collection 42 of cells, and the collection 45 or 46 of cells can be disposed.

Figure 10:
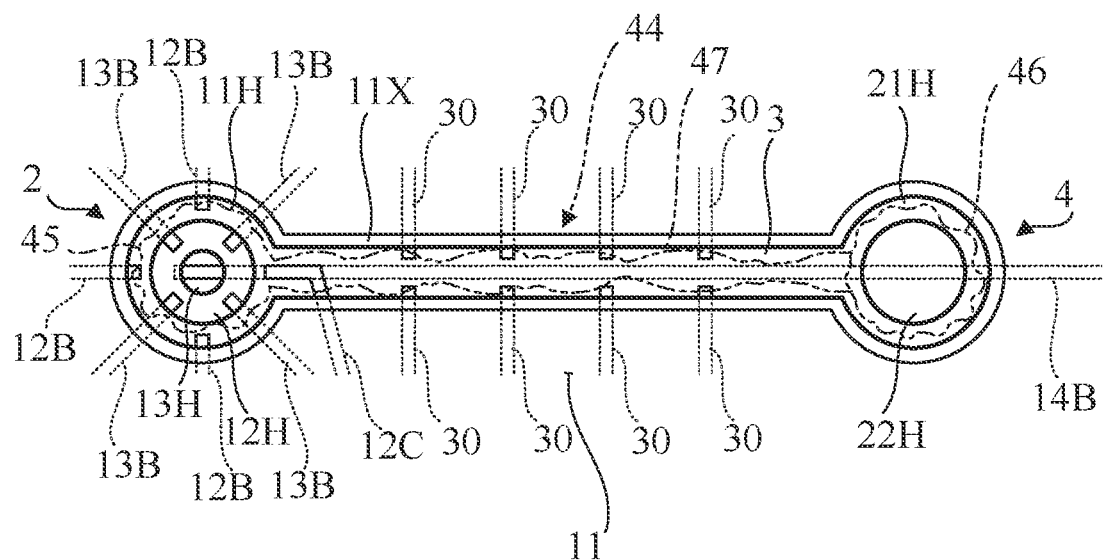
FIG. 10 is an enlarged plan view, similar to FIG. 8, of a part of the extracellular potential measurement device in which an example of a sample is disposed.

FIG. 10 shows measurement of potentials of sample 44 as an example of measurement of potentials of samples. The collections 45 and 46 of cells are deployed in the recesses 2 and 4, respectively, and the axon 47 is deployed in the groove 3.

The bottom of the collection 45 of cells is brought into contact with the end of the electrode wire 14B at the bottom of the recess 2. Ends of the electrode wires 12B, 12C, and 13B exposed in the recess 2 can be in contact with the collection 45 of cells, and as long as they are in contact with the collection 45 of cells, the potential at each point of the collection 45 of cells can be measured through the electrode wires 12B, 12C, and 13B.

In addition, ends of the axon electrode wires 30 exposed in the groove 3 can be in contact with the axon 47 located in the groove 3, and as long as they are in contact with the axon 47, the potential at each point of the axon 47 can be measured through the axon electrode wires 30. In measuring potentials of the axon as well as measuring potentials of the collection 45 of cells, for example, the electrode wire 14B can be used as the reference electrode, but any one of the other electrode wires can also be used as a reference electrode.

According to the extracellular potential measurement device 1, in addition to potentials of a collection of cells, potentials of an axon extending from the collection of cells can be measured. By analyzing the potentials, it is possible to study in vitro models that are useful for estimating signal transduction in neurons in vivo, and to evaluate, for example, drug effects and/or side effects on neurons.

Only one axon electrode wire 30 may be provided. However, in this embodiment, multiple axon electrode wires 30 are provided, and potentials at multiple points in the length direction of the axon can be measured, enabling more detailed analysis.

Figure 11:
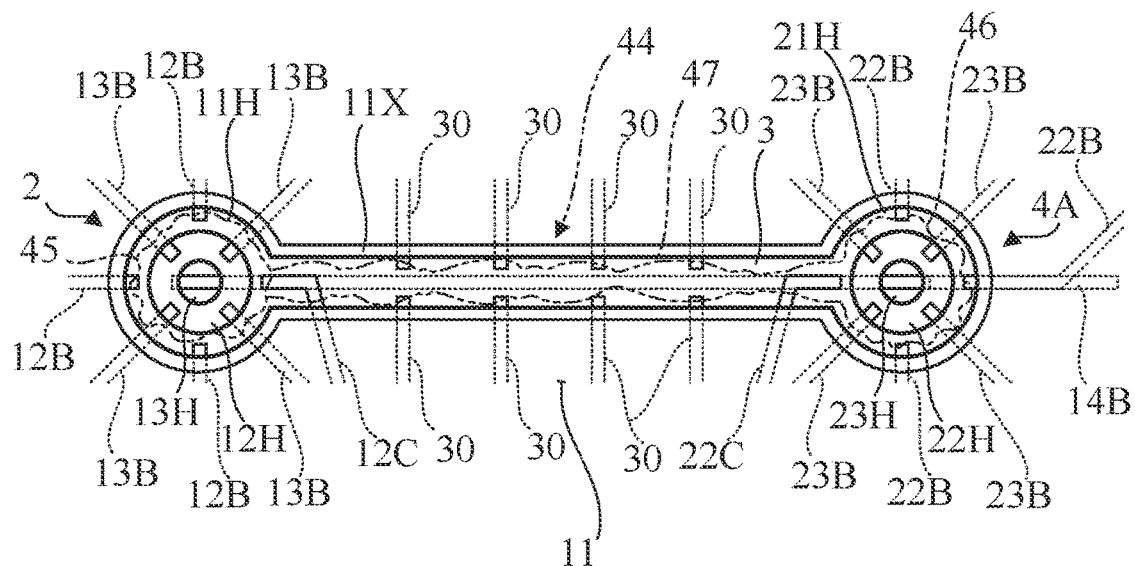
FIG. 11 is an enlarged plan view, similar to FIG. 8, of a part of an extracellular potential measurement device according to a modification of the embodiment of the present invention.

FIG. 11 is an enlarged plan view, similar to FIG. 8, of a part of an extracellular potential measurement device according to a modification of the embodiment. In this modification, potentials of both collections 45 and 46 of cells of sample 44 can be measured.

As shown in FIG. 11, this modification has a second recess 4A with electrodes instead of the recess 4 without electrodes. The second recess 4A is formed by an opening 21H that penetrates the insulating film 11, an opening 22H that penetrates the insulating film 12, and an opening 23H that penetrates the insulating film 13. In the second recess 4A, a collection 46 of cells is disposed in order to measure potentials of the collection 46 of cells. The openings 21H, 22H, and 23H forming the second recess 4A will be hereinafter referred to as second openings.

When the plurality of insulating films 11, 12, and 13 are stacked one on top of the other, the second openings 21H, 22H, and 23H form a second recess 4A that has an almost cone-shape or bowl-shape with a varying size reducing downward. However, the shapes of the openings 21H, 22H, and 23H are not limited to circular, but can be other shapes. The second opening 21H of the second recess 4A is connected to the groove 3.

Therefore, in this modification, the sheet 10 formed by the insulating film 11, 12, 13, and 14 and the adhesive layers 11A, 12A, and 13A has a recess 2, a groove 3 connected to the recess 2, and a second recess 4A connected to the groove 3.

This modification further has multiple second electrode wires 22B, 22C, and 23B disposed in multiple heights, i.e., multiple layers of the sheet 10. Each electrode wire is interposed between upper and lower insulating films. The second electrode wires 22B, 22C, and 23B are used to measure electric potentials at multiple points in different heights of the collection 46 of cells. Each of the second electrode wires is formed from an electroconductive material with high conductivity that has as little effect as possible on cells. For example, the second electrode wires are formed from gold-plated copper wires.

An end of each of the second electrode wires are located near the second opening in the insulating film immediately below it and is exposed in the second recess 4A. More specifically, the second electrode wires 22B and 22C are formed on the insulating film 12, and ends of the second electrode wires 22B and 22C are located near the opening 22H of the insulating film 12 immediately below the second electrode wires 22B and 22C, and are exposed through the upper opening 21H. The second electrode wires 23B are formed on the insulating film 13, and ends of the second electrode wires 23B are located near the opening 23H in the insulating film 13 immediately below the second electrode wire 23B, and are exposed through the upper openings 21H and 22H.

The second electrode wires 22B correspond to the electrode wires 12B associated with the recess 2, and the second electrode wire 22C corresponds to the electrode wire 12C associated with the recess 2. The second electrode wires 23B correspond to the electrode wires 13B associated with the recess 2. The details of the second electrode wires 22B, 22C, and 23B will be understood by referring to the description of electrode wires 12B, 12C, and 13B.

The electrode wire 14B traverses the entirety of the opening 23H in the second-lowermost-layer insulating film 13 in one direction. More specifically, the electrode wire 14B extends along a diameter of the circular second opening 23H and traverses the second opening 23H. The electrode wire 14B is exposed through the upper second openings 21H, 22H, and 23H. In measuring potentials of the collection 46 of cells as well as measuring potentials of the collection 45 of cells, for example, electrode wire 14B can be used as a reference electrode, but any one of the other electrode wires can also be used as a reference electrode.

The bottom of the collection 46 of cells is brought into contact with the end of the electrode wire 14B at the bottom of the second recess 4A. Ends of the second electrode wires 22B, 22C, and 23B exposed in the second recess 4A can be in contact with the collection 46 of cells, and as long as they are in contact with the collection 46 of cells, the potential at each point of the collection 46 of cells can be measured through the second electrode wires 22B, 22C, and 23B.

In this modification, a three-dimensional second collection 46 of cells is stored in the second recess 4A with a varying size reducing downward, which is provided by overlapping the second openings 21H, 22H, and 23H of the multiple insulating films 11, 12, and 13 stacked. An end of each of the second electrode wires 22B, 22C, and 23B interposed between upper and lower insulating films is located near the second opening of the insulating film immediately below it and is exposed in the second recess 4A, so that ends of the multiple second electrode wires 22B, 22C, and 23B can be in contact with the three-dimensional second collection of cells. The multiple second electrode wires 22B, 22C, and 23B are arranged in multiple heights, i.e., in multiple layers, so that electric potentials at multiple points in different heights of the second collection of cells can be measured.

Thus, potentials at multiple points of the two collections 45 and 46 of cells and the axon 47 between them can be measured. By analyzing the potentials, it is possible to study models of neuronal signal transduction in vivo, and in particular, interaction between the two collections of cells.

Since this modification has multiple second electrode wires 22B, 22C, and 23B, the plan view of the entirety of the extracellular potential measurement device, especially the arrangement of the axon electrode wires 30, is different from FIG. 2 (the second recess 4A is located at the position of the recess 4 in FIG. 2). However, by devising the pattern of the electrode wires including the axon electrode wires and the second electrode wires, it is possible to arrange the second electrode wires as in the modification.

Figure 12:
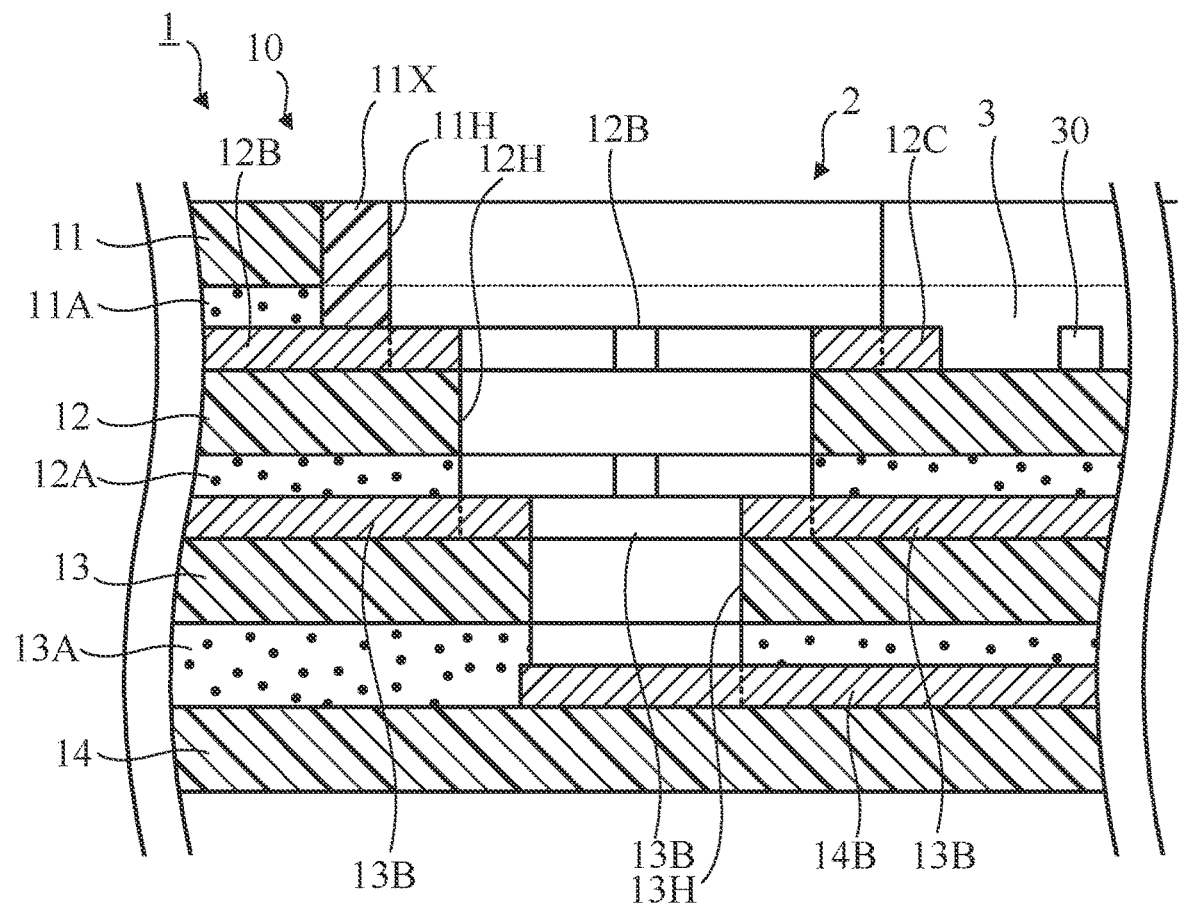
FIG. 12 is a cross-sectional view of an extracellular potential measurement device according to another modification of the embodiment of the present invention.

FIG. 12 is a cross-sectional view of an extracellular potential measurement device according to another modification of the present invention. In this modification, each of the electrode wires 12B, 12C, and 13B terminates at the edge, i.e., the inner peripheral surface of the openings 12H, 13H in the insulating films 12 and 13 immediately below the electrode wires. As can be clearly understood from comparison with FIG. 1, exposed portions of the electrode wires 12B, 12C, and 13B in the recesses 2 are increased, which increases the probability of contact with the collection of cells.

The present invention has been shown and described with reference to preferred embodiments thereof. However, it will be understood by those skilled in the art that various changes in form and detail may be made without departing from the scope of the invention as defined by the claims. Such variations, alterations, and modifications are intended to be encompassed in the scope of the present invention.

For example, the number of insulating films, the ratio of thicknesses of the multiple insulating films, the ratio of sizes of the multiple openings, the number, thickness, arrangement, and other details of the electrode wires including the axon electrode wires and the second electrode wires are not limited to the above-described embodiment and modifications.

In addition to the recess 2 and the second recess 4A shown in FIG. 11, more recesses and grooves connecting the recesses can be provided in an extracellular potential measurement device. Collection of cells and axons may be located in the recesses and grooves, respectively, and the potentials of these cells and axons may be measured.

Aspects of the present invention are also set out in the following numbered clauses:

Clause 1. An extracellular potential measurement device including:
multiple insulating films each of which is made from an electric insulating material, the insulating films being stacked and bonded to each other; and
multiple electrode wires each of which is made from an electroconductive material, the electrode wires being arranged in multiple heights,
each of the electrode wires being interposed between an upper insulating film and a lower insulating film,
each of the insulating films, except for a lowermost insulating film, having an opening penetrating the insulating film,
the opening in a lower insulating film having a size that is less than that of the opening in an upper insulating film, the openings in the insulating films being overlapped to form a recess having a size reducing downward, the recess being adapted to store a collection of cells,
each of the electrode wires having an end that is located near an opening in an insulating film that is immediately below the electrode wire, the ends being exposed in the recess.

Clause 2. The extracellular potential measurement device according to clause 1, further comprising an electrode wire made from an electric insulating material and interposed between the lowermost insulating film and a second lowermost insulating film, wherein an end of the electrode wire interposed between the lowermost insulating film and the second lowermost insulating film traverses the opening of the second lowermost insulating film entirely in one direction.

According to this clause, the end of this electrode wire traverses the entirety of the opening of the second lowermost insulating film, i.e., the bottom of the recess, in one direction. Accordingly, a large area of the end of the electrode wire is exposed in the recess, and the collection of cells located in the recess is likely to come into contact with the end of the electrode wire. The electrode wire, which has a high probability of contacting a collection of cells, can be preferably used as a reference electrode, for example.

Clause 3. The extracellular potential measurement device according to clause 1 or 2, wherein an uppermost insulating film has a groove penetrating the uppermost insulating film, the groove being adapted to store a linear axon extending from the collection of cells, the groove being connected to the recess, the extracellular potential measurement device further including at least one axon electrode wire, an end of the axon electrode wire is exposed in the groove so as to be brought into contact with the axon.

According to this clause, in addition to potentials of a collection of cells, potentials of an axon extending from the collection of cells can be measured. By analyzing the potentials, it is possible to study in vitro models that are useful for estimating signal transduction in neurons in vivo, and to evaluate, for example, drug effects and/or side effects on neurons.

Clause 4. The extracellular potential measurement device according to clause 3, further including multiple second electrode wires each of which is made from an electroconductive material, the second electrode wires being arranged in multiple heights, each of the second electrode wires being interposed between an upper insulating film and a lower insulating film, each of the insulating films, except for the lowermost insulating film, having a second opening penetrating the insulating film, the second opening in a lower insulating film having a size that is less than that of the second opening in an upper insulating film, the second openings in the insulating films being overlapped to form a second recess having a size reducing downward, the second recess being adapted to store a second collection of cells to which the axon is connected, the second recess being connected to the groove, each of the second electrode wires having an end that is located near a second opening in an insulating film that is immediately below the second electrode wire, the ends of the second electrode wires being exposed in the second recess.

According to this clause, a three-dimensional second collection of cells is stored in the second recess with a varying size reducing downward, which is provided by overlapping the second openings of the multiple insulating films stacked. An end of each of the second electrode wires interposed between upper and lower insulating films is located near the second opening of the insulating film immediately below it and is exposed in the second recess, so that ends of the multiple second electrode wires can be in contact with the three-dimensional second collection of cells. The multiple second electrode wires are arranged in multiple heights, i.e., in multiple layers, so that electric potentials at multiple points in different heights of the second collection of cells can be measured. Thus, potentials at multiple points of the two collections of cells and the axon therebetween can be measured. By analyzing the potentials, it is possible to study models of neuronal signal transduction in vivo, and in particular, interaction between the two collections of cells.

Clause 5. The extracellular potential measurement device according to any one of clauses 1 to 4, wherein the upper insulating film and the lower insulating film are bonded together with an adhesive.

According to this clause, the extracellular potential measurement device can be easily manufactured.

Clause 6. An extracellular potential measurement device including:

a sheet including multiple insulating films each of which is made from an electric insulating material, the insulating films being stacked and bonded to each other, the sheet further including a recess adapted to store a collection of cells and a groove connected to the recess, the groove being adapted to store a linear axon extending from the collection of cells; and multiple electrode wires interposed between the insulating films of the sheet, multiple electrode wires having ends exposed in the recess so as to be brought into contact with the collection of cells, at least one electrode wire having an end exposed in the groove so as to be brought into contact with the axon.

Clause 7. The extracellular potential measurement device according to clause 6, wherein the electrode wires that have ends exposed in the recess are arranged in multiple heights.

According to this clause, electric potentials at multiple points in different heights of a three-dimensional collection of cells can be measured.

Clause 8. The extracellular potential measurement device according to clause 7, wherein each of the insulating films, except for a lowermost insulating film, has an opening penetrating the insulating film, the opening in a lower insulating film having a size that is less than that of the opening in an upper insulating film, the openings in the insulating films being overlapped to form the recess having a size reducing downward, each of the ends of the electrode wires exposed in the recess being located near an opening in an insulating film that is immediately below the electrode wire.

According to this clause, a three-dimensional collection of cells is stored in the recess with a varying size reducing downward, which is provided by overlapping the openings of the multiple insulating films stacked. An end of each of the electrode wires interposed between upper and lower insulating films is located near the opening in the insulating film immediately below it and is exposed in the recess. Accordingly, ends of the multiple electrode wires can be in contact with at multiple points in different heights of the three-dimensional collection of cells.

Clause 9. The extracellular potential measurement device according to any one of clauses 6 to 8, further including multiple second electrode wires interposed between the insulating films of the sheet, the sheet including a second recess adapted to store a second collection of cells to which the axon is connected, the second recess being connected to the groove, each of the second electrode wires having an end exposed in the second recess so as to be brought into contact with the second collection of cells.

According to this clause, electric potentials at multiple points of the two collections of cells and the axon therebetween can be measured. By analyzing the potentials, it is possible to study in vitro models that are useful for estimating signal transduction in neurons in vivo, and in particular, interaction between the two collections of cells.

Clause 10. The extracellular potential measurement device according to clause 9, wherein the second electrode wires are arranged in multiple heights.

According to this clause, electric potentials at multiple points in different heights of a three-dimensional second collection of cells can be measured.

Clause 11. The extracellular potential measurement device according to clause 10, wherein each of the insulating films, except for the lowermost insulating film, has a second opening penetrating the insulating film, the second opening in a lower insulating film having a size that is less than that of the second opening in an upper insulating film, the second openings in the insulating films being overlapped to form the second recess having a size reducing downward, each of the second electrode wires having an end that is located near a second opening in an insulating film that is immediately below the second electrode wire, the ends of the second electrode wires being exposed in the second recess.

According to this clause, a three-dimensional second collection of cells is stored in the second recess with a varying size reducing downward, which is provided by overlapping the second openings of the multiple insulating films stacked. An end of each of the second electrode wires interposed between upper and lower insulating films is located near the second opening of the insulating film immediately below it and is exposed in the second recess, so that ends of the multiple second electrode wires can be easily in contact with multiple points in different heights of the three-dimensional second collection of cells.

The invention claimed is:

1. An extracellular potential measurement device comprising:
   multiple insulating films each of which is made from an electric insulating material, the insulating films being stacked and bonded to each other; and
   multiple electrode wires each of which is made from an electroconductive material, the electrode wires being arranged in multiple heights,
   each of the electrode wires being interposed between an upper insulating film and a lower insulating film,
   each of the insulating films, except for a lowermost insulating film, having an opening penetrating the insulating film,
   the opening in a lower insulating film having a size that is less than that of the opening in an upper insulating film, the openings in the insulating films being overlapped to form a recess having a size reducing downward, the recess being adapted to store a collection of cells,
   each of the electrode wires having an end that is located near an opening in an insulating film that is immediately below the electrode wire, the ends being exposed in the recess.

2. The extracellular potential measurement device according to claim 1, further comprising an electrode wire made from an electric insulating material and interposed between the lowermost insulating film and a second lowermost insulating film, wherein an end of the electrode wire interposed between the lowermost insulating film and the second lowermost insulating film traverses the opening of the second lowermost insulating film entirely in one direction.

3. The extracellular potential measurement device according to claim 2, wherein an uppermost insulating film has a groove penetrating the uppermost insulating film, the groove being adapted to store a linear axon extending from the collection of cells, the groove being connected to the recess,
   the extracellular potential measurement device further comprising at least one axon electrode wire, an end of the axon electrode wire is exposed in the groove so as to be brought into contact with the axon.

4. The extracellular potential measurement device according to claim 3, further comprising multiple second electrode wires each of which is made from an electroconductive material, the second electrode wires being arranged in multiple heights,
   each of the second electrode wires being interposed between an upper insulating film and a lower insulating film,
   each of the insulating films, except for the lowermost insulating film, having a second opening penetrating the insulating film,
   the second opening in a lower insulating film having a size that is less than that of the second opening in an upper insulating film, the second openings in the insulating films being overlapped to form a second recess having a size reducing downward, the second recess being adapted to store a second collection of cells to which the axon is connected, the second recess being connected to the groove,
   each of the second electrode wires having an end that is located near a second opening in an insulating film that is immediately below the second electrode wire, the ends of the second electrode wires being exposed in the second recess.

5. The extracellular potential measurement device according to claim 1, wherein an uppermost insulating film has a groove penetrating the uppermost insulating film, the groove being adapted to store a linear axon extending from the collection of cells, the groove being connected to the recess,
   the extracellular potential measurement device further comprising at least one axon electrode wire, an end of the axon electrode wire is exposed in the groove so as to be brought into contact with the axon.

6. The extracellular potential measurement device according to claim 5, further comprising multiple second electrode wires each of which is made from an electroconductive material, the second electrode wires being arranged in multiple heights,
   each of the second electrode wires being interposed between an upper insulating film and a lower insulating film,
   each of the insulating films, except for the lowermost insulating film, having a second opening penetrating the insulating film,
   the second opening in a lower insulating film having a size that is less than that of the second opening in an upper insulating film, the second openings in the insulating films being overlapped to form a second recess having a size reducing downward, the second recess being adapted to store a second collection of cells to which the axon is connected, the second recess being connected to the groove,
   each of the second electrode wires having an end that is located near a second opening in an insulating film that is immediately below the second electrode wire, the ends of the second electrode wires being exposed in the second recess.

7. The extracellular potential measurement device according to claim 1, wherein the upper insulating film and the lower insulating film are bonded together with an adhesive.

8. An extracellular potential measurement device comprising:
   a sheet comprising multiple insulating films each of which is made from an electric insulating material, the insulating films being stacked and bonded to each other, the sheet further comprising a recess adapted to store a collection of cells and a groove connected to the recess, the groove being adapted to store a linear axon extending from the collection of cells; and
   multiple electrode wires interposed between the insulating films of the sheet, multiple electrode wires having ends exposed in the recess so as to be brought into contact with the collection of cells, at least one electrode wire having an end exposed in the groove so as to be brought into contact with the axon.

9. The extracellular potential measurement device according to claim 8, wherein the electrode wires that have ends exposed in the recess are arranged in multiple heights.

10. The extracellular potential measurement device according to claim 9, wherein each of the insulating films, except for a lowermost insulating film, has an opening penetrating the insulating film, the opening in a lower insulating film having a size that is less than that of the opening in an upper insulating film, the openings in the insulating films being overlapped to form the recess having a size reducing downward, each of the ends of the electrode wires exposed in the recess being located near an opening in an insulating film that is immediately below the electrode wire.

11. The extracellular potential measurement device according to claim 8, further comprising multiple second electrode wires interposed between the insulating films of the sheet, the sheet comprising a second recess adapted to store a second collection of cells to which the axon is connected, the second recess being connected to the groove, each of the second electrode wires having an end exposed in the second recess so as to be brought into contact with the second collection of cells.

12. The extracellular potential measurement device according to claim 11, wherein the second electrode wires are arranged in multiple heights.

13. The extracellular potential measurement device according to claim 12, wherein each of the insulating films, except for a lowermost insulating film, has a second opening penetrating the insulating film, the second opening in a lower insulating film having a size that is less than that of the second opening in an upper insulating film, the second openings in the insulating films being overlapped to form the second recess having a size reducing downward, each of the second electrode wires having an end that is located near a second opening in an insulating film that is immediately below the second electrode wire, the ends of the second electrode wires being exposed in the second recess.

14. The extracellular potential measurement device according to claim 8, further comprising an electrode wire made from an electric insulating material and interposed between a lowermost insulating film and a second lowermost insulating film, wherein an end of the electrode wire interposed between the lowermost insulating film and the second lowermost insulating film traverses the opening of the second lowermost insulating film entirely in one direction.

* * * * *